(12) United States Patent
Kelly

(10) Patent No.: US 6,288,260 B1
(45) Date of Patent: Sep. 11, 2001

(54) PROCESS FOR MAKING 2-ALKYL-3-HYDROXYBENZOIC ACIDS

(75) Inventor: Martha Jean Kelly, Norristown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/455,996

(22) Filed: Dec. 7, 1999

Related U.S. Application Data

(60) Provisional application No. 60/111,310, filed on Dec. 8, 1998.

(51) Int. Cl.$^7$ .................... C07C 255/50; C07C 69/88; C07C 65/01
(52) U.S. Cl. .................... 558/365; 558/377; 558/423; 560/67; 562/475
(58) Field of Search .................... 558/423, 365, 558/377; 560/67; 562/475

(56) References Cited

U.S. PATENT DOCUMENTS 5,530,028  6/1996  Lidert et al. .................... 514/649

FOREIGN PATENT DOCUMENTS 0 831 083 A1  3/1998  (EP) .

OTHER PUBLICATIONS

Allen J. Guildford and Ralph W. Turner, J. Chem.Soc., Chem.Commun, 1983.

M.P.S. Ishar, A. Wali, and R. P. Gandhi, J. Chem. Soc., Pekin Trans 1990.

Kozikowski, et al., J. C. S. Chem. Comm. (1977), 582.

Kozikowski, et al., J. Org. Chem., 43, 2083 (1978).

*Primary Examiner*—Floyd D. Higel
*Assistant Examiner*—Ebenezer Sackey
(74) *Attorney, Agent, or Firm*—Clark B. Carpenter

(57) ABSTRACT

A two step process is described for making 2-alkyl-3-hydroxybenzoic acids or derivatives of benzoic acids by first reacting an allenyl ester or equivalent with furan followed by the ring-opening reaction of the derived bicyclo intermediate with base. The benzoic acids thus prepared are useful intermediates for the preparation of agricultural and pharmaceutical materials.

9 Claims, No Drawings

PROCESS FOR MAKING 2-ALKYL-3-HYDROXYBENZOIC ACIDS

This is a nonprovisional application of prior pending provisional application Ser. No. 60/111,310 filed Dec. 8, 1998.

This invention relates to a new and convenient two step process for making 2-alkyl-3-hydroxybenzoic acids or derivatives of benzoic acids by first reacting an allenyl ester or equivalent with furan, followed by the ring-opening reaction of the derived bicyclo intermediate with base. The benzoic acids thus prepared are useful intermediates for the preparation of agricultural and pharmaceutical materials.

Although various routes are known to such benzoic acids, for example, conversion of an amino substituted benzoic acid or ester to an alkoxy or hydroxy substituted benzoic acid or ester using a diazotization reaction as described in U.S. Pat. No. 5,530,028, and processes leading to optionally substituted hydroxybenzoic and alkoxybenzoic acids as well as optionally substituted hydroxybenzonitriles and alkoxybenzonitriles from substituted 2,6-dihalobenzenes as described in EP 0 831 083 A, there is a continuing need to provide these kinds of acids and nitrites at lower cost and higher purity. The present invention provides an advantageous route to produce the desired benzoic acids, esters and benzonitriles. Although Kozikowski, et al. in both *J. C. S. Chem. Comm.* (1977), 582 and *J. Org. Chem.*, 43, 2083 (1978) describe the reaction of heterocycles, including furan, with allenes which must be substituted in both the 1 and 3 position with electron withdrawing groups, the process of the present invention is neither disclosed nor suggested.

I have found conditions which allow the preparation of substituted hydroxybenzoic acids and derivatives thereof by reaction of substituted allenes with furan in a Diels-Alder reaction followed by treatment of the resulting cycloadduct with base in a second step. The process of the present invention avoids the problems associated with the use of potentially unstable diazonium salts or cyanation conditions in multi-step processes.

In summary, the present invention provides a process to prepare a compound of formula (I) comprising the reaction of furan with a substituted allene of formula (II) to form a bicyclic compound of formula (III) in a first step

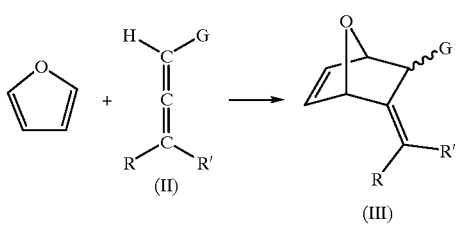

followed by reaction of the bicyclic compound of formula (III) with a base to form the compound of formula (I) in a second step

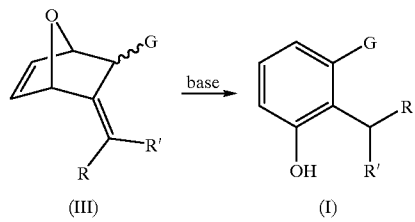

wherein
G is carboxy, alkoxycarbonyl or cyano and
R and R' are each independently a hydrogen atom or alkyl.

In this invention, the term alkyl refers to either a straight chain $(C_1-C_4)$alkyl such as, but not limited to, methyl, ethyl, n-propyl and n-butyl or a branched chain $(C_3-C_4)$alkyl such as, but not limited to, isopropyl and isobutyl. Alkoxycarbonyl refers to a linear $(C_1-C_4)$alkoxy or a branched $(C_3-C_4)$ alkoxy moiety attached to a carbonyl group and includes, for example, methoxycarbonyl, ethoxycarbonyl and isobutyloxycarbonyl.

In a preferred embodiment of this invention, G is carboxy, $(C_1-C_2)$alkoxycarbonyl or cyano, R is a hydrogen atom or $(C_1-C_3)$alkyl and R' is a hydrogen atom. In a more preferred embodiment, R is a hydrogen atom or methyl.

The first step of the process can be run using excess furan as the solvent. Alternatively, an inert solvent such as a chlorinated hydrocarbon, for example methylene chloride, an aliphatic ether, for example diethyl ether, a cyclic ether, for example tetrahydrofuran, or an aromatic hydrocarbon, for example toluene may also be present with a lesser quantity of furan. An antioxidant such as 2,6-di-tert-butyl-4-methylphenol (BHT) may also be added to prevent by-product formation. This step can be run under pressure or at atmospheric pressure. A catalyst is normally employed to facilitate this Diels-Alder condensation. Such catalyts include, but are not limited to, a Lewis acid such as zinc chloride, zinc iodide, aluminum trichloride, boron trifluoride, $Ti[OCH(CH_3)_2]_4$ or $ClTi[OCH(CH_3)_2]_3$, a lanthanide complex such as $Eu(fod)_3$, a mildly acidic solvent such as hexafluoroisopropanol, a metal exchanged zeolite such as CuI exchanged Y zeolite, or lithium perchlorate in ether. Reaction temperature for the first step can range from −78° C. to 150° C., preferably from 0° C. to 100° C., and more preferably from 18° C. to 100° C.

The second step of the process can be carried out with a variety of bases such as, but not limited to, sodium hydroxide, potassium hydroxide, potassium tert-butoxide, sodium hydride, lithium hexamethyldisilazane and the like. The temperature can range from −78° C. to 100° C., preferably from 0° C. to 100° C.

The allenic esters or their equivalents can be made using the procedure described by Lang et al. in *Organic Synthesis*, M. F. Semmelhack, ed., 62, 202 (1984), using Wittig chemistry. There are several other possible methods which may make the allenic ester or its equivalent. Many routes to compounds of this type are given by Landor in *The Chemistry of Allenes*, Landor, ed., 1, 131–154 (1982), Academic Press. One approach is to start with an acetoacetate, convert it to the corresponding enol phosphate or vinyl chloride, then eliminate this group to form the allenyl ester. A second possible method would be to react sodium acetylide with an alkyl chloroacetate to make the alkyl 3-butynoate. These compounds have been reported to isomerize to the allenyl ester in excellent yields. The reaction of propargyl halides with cyanide (in the presence of copper) followed by isomerization would give the allenylnitrile. There are also references a palladium catalyzed carbonylation of propargylic carbonates. These reactions are summarized in Scheme 1 where X is chloro or $OP(=O)(OR)_2$, Ph is phenyl and R is alkyl.

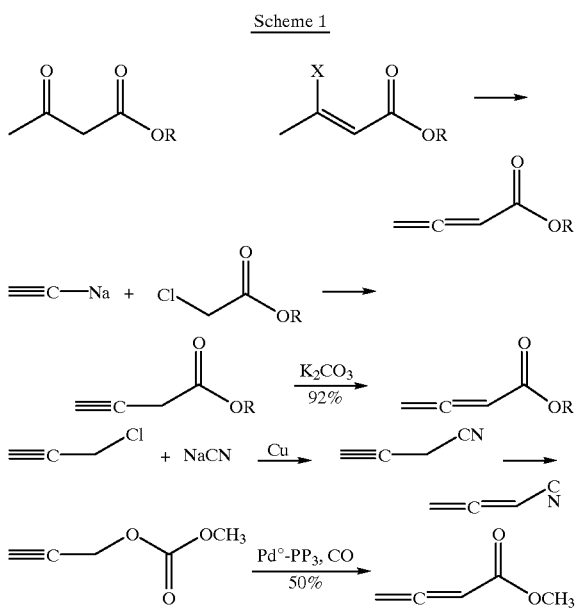

The following examples are given in order to further guide the practitioner of this invention.

EXAMPLE 1

Preparation of Ethyl 2,3-Butadienoate

Ethyl 2,3-butadienoate was prepared according to the method described in Lang et al. vide supra. This ester has a strong, unpleasant odor.

EXAMPLE 2

Preparation of 2-Ethoxycarbonyl-3-methylene-7-oxa-5-norbornene via the Diels-Alder Reaction Ethyl 2,3-butadienoate (0.84 g, 7.5 mmol) and 2.52 g of furan (37 mmol) were combined in a flask under nitrogen and cooled to 0° C. Anhydrous zinc chloride (0.25 g, 1.8 mmol) was added, then the reaction mixture was warmed to room temperature and stirred overnight. NMR analysis indicated that the reaction was complete. Toluene and dilute HCl were added. A black lump of material separated. The toluene and water phases were decanted. The toluene phase was washed with water, filtered and rotovapped. Methylene chloride and aqueous HCl were added to the black solids which dissolved. The methylene chloride phase was washed with water, combined with the rotovapped toluene phase and stripped. A total of 1.18 g of a light brown liquid was obtained.

The reaction was also run under similar conditions except for the substitution of lithium perchlorate in ether for the zinc chloride catalyst.

EXAMPLE 3

Preparation of 3-Hydroxy-2-methylbenzoic Acid

The cycloadduct (1.05 g) from Example 2, 1.80 g of potassium tert-butoxide and 9 mL of tert-butanol were combined and refluxed a total of 9 hours. The reaction mixture was poured into water. Toluene was added. The toluene phase was washed twice with dilute sodium hydroxide solution. The combined aqueous phases were acidified with HCl, then extracted several times with t-butyl acetate. The n-butyl acetate was stripped, and the product dried in a vacuum oven to give 0.87 g of 3-hydroxy-2-methylbenzoic acid, 94% purity, 79% yield.

I claimed:

1. A process to prepare a compound of formula (I) comprising the reaction of furan with a substituted allene of formula (II) to form a bicyclic compound of formula (III) in a first step

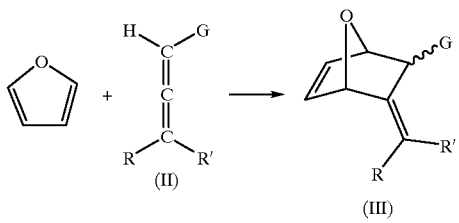

followed by reaction of the bicyclic compound of formula (III) with a base to form the compound of formula (I) in a second step

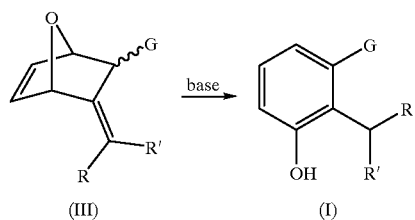

wherein

G is carboxy, alkoxycarbonyl or cyano and

R and R' are each independently a hydrogen atom or alkyl.

2. The process of claim 1 wherein G is carboxy, $(C_1-C_2)$ alkoxycarbonyl or cyano, R is a hydrogen atom or $(C_1-C_3)$ alkyl and R' is a hydrogen atom.

3. The process of claim 2 wherein R is a hydrogen atom or methyl.

4. The process of claim 1 further comprises the use of a solvent in the first step, said solvent being selected from the group consisting of excess furan, a chlorinated hydrocarbon, an aliphatic ether, a cyclic ether and an aromatic hydrocarbon.

5. The process of claim 4 wherein the solvent is excess furan.

6. The process of claim 1 further comprising the use of 2,6-di-tert-butyl-4-methylphenol as an antioxidant in the first step.

7. The process of claim 1 further comprising the use of a catalyst in the first step that is selected from the group consisting of a Lewis acid, a lanthanide complex, a mildly acidic solvent, a metal exchanged zeolite and lithium perchlorate in ether.

8. The process of claim 7 wherein the catalyst is zinc chloride, zinc iodide, aluminum trichloride, boron trifluoride, Ti[OCH(CH$_3$)$_2$]$_4$, ClTi[OCH(CH$_3$)$_2$]$_3$, Eu(fod)$_3$, hexafluoroisopropanol, CuI exchanged Y zeolite or lithium perchlorate in ether.

9. The process of claim 1 wherein the base used in the second step is sodium hydroxide, potassium hydroxide, potassium tert-butoxide, sodium hydride or lithium hexamethyldisilazane.

* * * * *